(12) United States Patent
Emerson

(10) Patent No.: US 6,860,265 B1
(45) Date of Patent: Mar. 1, 2005

(54) INSUFFLATION-EXSUFFLATION SYSTEM FOR REMOVAL OF BRONCHO-PULMONARY SECRETIONS WITH AUTOMATIC TRIGGERING OF INHALATION PHASE

(75) Inventor: George P. Emerson, Arlington, MA (US)

(73) Assignee: J.H. Emerson Company, Cambridge, MA (US)

( * ) Notice: Subject to any disclaimer, the term of this patent is extended or adjusted under 35 U.S.C. 154(b) by 18 days.

(21) Appl. No.: 10/657,405

(22) Filed: Sep. 8, 2003

(51) Int. Cl.$^7$ ................................................ A62B 7/10
(52) U.S. Cl. ........................... 128/205.12; 128/205.19; 128/204.23
(58) Field of Search ..................... 128/204.21, 204.23, 128/204.26, 205.12, 205.18, 205.19; 600/41–43; 482/13

(56) References Cited

U.S. PATENT DOCUMENTS

| | | | | |
|---|---|---|---|---|
| 1,044,031 A | * | 11/1912 | Daxger | 128/205.19 |
| 1,169,995 A | * | 2/1916 | Prindle | 128/205.19 |
| 1,358,893 A | * | 11/1920 | Stolle | 128/204.25 |
| 2,364,626 A | * | 12/1944 | Emerson | 128/204.25 |
| 2,428,451 A | * | 10/1947 | Emerson | 128/205.13 |
| 2,468,741 A | * | 5/1949 | Emerson | 128/204.25 |
| 2,481,299 A | * | 9/1949 | Emerson | 128/204.25 |

(List continued on next page.)

OTHER PUBLICATIONS

U.S. Appl. No. 10/657,424, filed Sep, 8, 2003, Emerson.

*Primary Examiner*—Aaron J. Lewis
(74) *Attorney, Agent, or Firm*—Iandiorio & Teska

(57) ABSTRACT

An improved insufflation-exsufflation system for removal of broncho-pulmonary secretions with automatic triggering of inhalation phase includes a conduit for connection to a patient's airway; a pressure source with a positive pressure port and a negative pressure port; a switching device selectively connecting the conduit to the positive pressure port, the negative pressure port and the dwell port; the sensor system for sensing an inhalation by the patient; and a controller system for driving the switching device to connect the conduits sequentially to the positive port, the negative port and the dwell port and to return again to the positive port in response to the sensor system sensing an inhalation by the patient while the conduit is connected to the dwell port.

7 Claims, 4 Drawing Sheets

U.S. PATENT DOCUMENTS

| | | | |
|---|---|---|---|
| 2,512,621 A | | 6/1950 | Emerson |
| 2,774,347 A | * | 12/1956 | Emerson ................. 601/43 |
| 2,774,348 A | * | 12/1956 | Emerson ................. 601/43 |
| 2,853,998 A | * | 9/1958 | Emerson ................. 601/44 |
| 2,861,568 A | * | 11/1958 | Quilter et al. ........ 128/201.23 |
| 2,914,064 A | * | 11/1959 | Sandelowsky ........ 128/205.19 |
| 2,918,917 A | * | 12/1959 | Emerson ............... 128/205.19 |
| 3,357,428 A | * | 12/1967 | Carlson ................ 128/204.23 |
| 3,368,212 A | * | 2/1968 | Klyce, Jr. .................. 340/606 |
| 3,402,711 A | * | 9/1968 | Emerson ............... 128/204.28 |
| 3,653,379 A | | 4/1972 | Glenn |
| 3,768,468 A | * | 10/1973 | Cox ...................... 128/204.21 |
| 3,794,026 A | * | 2/1974 | Jacobs .................. 128/200.13 |
| 3,850,170 A | * | 11/1974 | Cox ...................... 128/204.24 |
| 3,976,064 A | * | 8/1976 | Wood et al. ........... 128/204.21 |
| 4,054,134 A | | 10/1977 | Kritzer |
| 4,062,358 A | | 12/1977 | Kritzer |
| 4,193,406 A | * | 3/1980 | Jinotti .................. 128/204.18 |
| 4,206,754 A | * | 6/1980 | Cox et al. ............. 128/204.21 |
| 4,273,120 A | * | 6/1981 | Oswell ................. 128/204.26 |
| 4,281,651 A | * | 8/1981 | Cox ...................... 128/204.23 |
| 4,393,869 A | * | 7/1983 | Boyarsky et al. ...... 128/204.18 |
| 4,565,194 A | * | 1/1986 | Weerda et al. ......... 128/204.23 |
| 4,592,741 A | | 6/1986 | Vincent |
| 4,595,004 A | | 6/1986 | Czech |
| 4,977,889 A | | 12/1990 | Budd |
| 5,127,398 A | * | 7/1992 | Stone .................... 128/204.18 |
| 5,280,784 A | | 1/1994 | Kohler |
| 5,311,862 A | * | 5/1994 | Blasdell et al. ........ 128/205.25 |
| 5,400,778 A | * | 3/1995 | Jonson et al. .......... 128/205.19 |
| 5,419,768 A | * | 5/1995 | Kayser ..................... 604/119 |
| 5,611,335 A | | 3/1997 | Makhoul et al. |
| 5,645,537 A | | 7/1997 | Powles et al. |
| 5,673,689 A | * | 10/1997 | Power ................... 128/205.18 |
| 5,829,429 A | | 11/1998 | Hughes |
| 5,850,835 A | * | 12/1998 | Takaki et al. .......... 128/204.18 |
| 5,893,361 A | | 4/1999 | Hughes |
| 5,988,166 A | * | 11/1999 | Hayek ................... 128/205.26 |
| 6,058,932 A | | 5/2000 | Hughes |
| 6,167,881 B1 | | 1/2001 | Hughes |
| 6,176,235 B1 | | 1/2001 | Benarrouch et al. |
| 6,209,540 B1 | * | 4/2001 | Sugiura et al. ........ 128/204.18 |
| 6,547,749 B2 | | 4/2003 | Hansen |
| 6,595,213 B2 | * | 7/2003 | Bennarsten ............ 128/205.19 |
| 6,694,978 B1 | | 2/2004 | Bennarsten |

\* cited by examiner

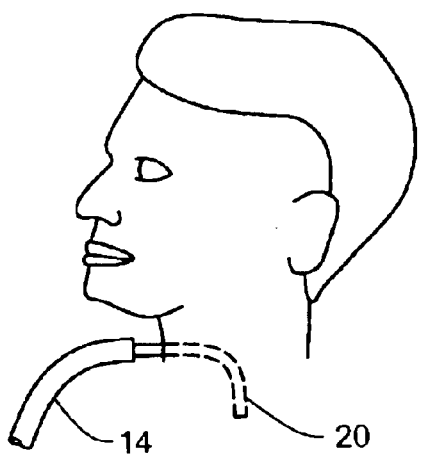
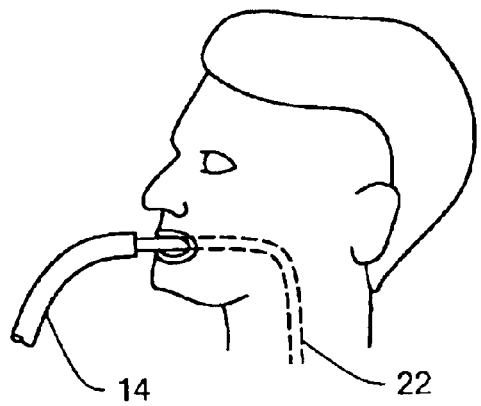
FIG. 2  FIG. 3
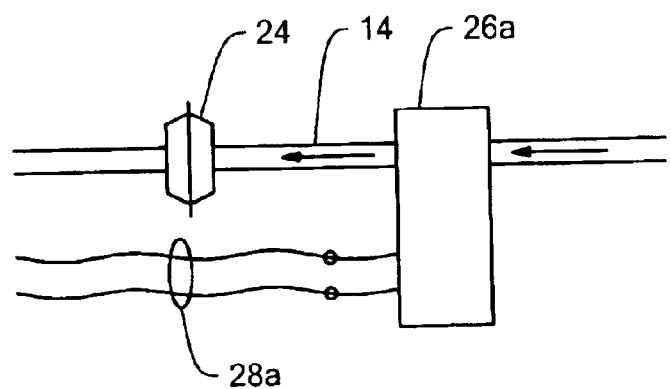
FIG. 4

INSUFFLATION-EXSUFFLATION SYSTEM FOR REMOVAL OF BRONCHO-PULMONARY SECRETIONS WITH AUTOMATIC TRIGGERING OF INHALATION PHASE

FIELD OF THE INVENTION

This invention relates to an improved insufflation-exsufflation system with automatic triggering of inhalation phase.

BACKGROUND OF THE INVENTION

The use of mechanical insufflation and exsufflation (MI-E) with negative pressure is a well-known technique for helping patients with an ineffective cough to remove secretions from the respiratory tract. Patients who can benefit from the technique include: post-polio, muscular dystrophy, spinal muscular atrophy (SMA), post-cardiac surgery, amyotropic lateral sclerosis (ALS), mechanically ventilated, or anyone with insufficient muscle strength to generate the high expiratory flows necessary for moving secretions up the tracheobronchial tree. The technique involves the use of a blower and valve, which, via a facemask, mouthpiece or adapter for a tracheal tube, alternately applies positive pressure first to inflate the lungs, then shifts rapidly to negative pressure to create a high expiratory flow.

During automatic operation of the device, the internal valve executes a sequence of pressures applied to the patient's airway: first positive pressure to inflate the lungs, then a shift to negative pressure to create a high exhalation flow. This sequence is typically repeated a number of times (anywhere from 2 to 6) in succession for a treatment. The timing of each phase is adjustable by the user. Also, the initiation of the sequence is begun by the user actuating a switch. Alternatively, the user may also initiate each phase by actuating a switch while in a manual mode.

One shortcoming of current MI-E devices is that the beginning of an inhalation phase (positive pressure to first inflate the lungs) is triggered by either the patient or the patient's caregiver actuating a switch to begin the cycling. If the sequence is begun while the patient is exhaling, or the patient is not ready for an inhalation from the device, the patient may find the first inhalation uncomfortable, and may even unconsciously block the flow of air into the lungs. This can limit the effectiveness of the treatment, since a full deep inhalation breath is necessary to achieve adequate exhalation flow. Typically a caregiver must "coach" the patient during a treatment, explaining when to inhale, to avoid this problem. Alternatively, the caregiver watches the patient's respiration in order to switch on the cycling when the patient begins to inhale. Another shortcoming of the current device is that it is difficult to use on very young pediatric patients, and on unconscious or uncooperative patients, where it is difficult to explain to the patient when to begin an inhalation.

Assist modes have been used on positive pressure ventilators, which "breathe" a patient by applying a positive pressure to the airway, usually via an endotracheal or tracheostomy tube. Such assist modes also detect the patient's inspiratory effort in order to trigger the delivery of a breath by the ventilator. More recently, the advent of bi-level Continuous Positive Airway Pressure (CPAP) devices to support patients with respiratory insufficiency has also resulted in the use of some means to detect when the patient has begun inhalation, in order to determine when to increase the pressure applied to the airway.

While automatic assist modes work well with positive pressure ventilators they are not easily applicable to insufflation-exsufflation systems. In positive pressure ventilators the slight negative pressure or flow created by a patient inhalation is used to trigger a delivery of positive pressure, the breath or inhalation, for the patient. Then the positive pressure is stopped as the patient exhales to atmospheric or slight positive pressure. Following this the next negative pressure or flow sensed when the patient again inhales can be used to trigger delivery of the next positive pressure. In contrast in insufflation-exsufflation systems after the inhale/positive pressure comes the exhale negative pressure. After the time set for the negative pressure the system will return to the positive pressure but on the basis of the existing negative pressure which may not be the negative pressure created by a patient inhalation, thereby losing synchronism with the normal breathing of the patient.

BRIEF SUMMARY OF THE INVENTION

It is therefore an object of this invention to provide an improved insufflation-exsufflation system for removal of broncho-pulmonary secretions.

It is a further object of this invention to provide such an improved insufflation-exsufflation system with reliable automatic triggering of the inhalation phase.

It is a further object of this invention to provide such an improved insufflation-exsufflation system, which is easier to synchronize with a patient's spontaneous breaths.

It is a further object of this invention to provide such an improved insufflation-exsufflation system, which increases inhalation volume for patients including unconscious, uncooperative, and pediatric patients.

It is a further object of this invention to provide such an improved insufflation-exsufflation system which is more comfortable for patients.

The invention results from the realization that an improved insufflation-exsufflation system for removal of broncho-pulmonary secretions with automatic triggering of inhalation phase can be effected by selectively connecting a patients breathing conduit to a positive pressure port, a negative pressure port and a dwell port, only after an inhalation of the patient has been sensed while the conduit is connected to the dwell port.

This invention features an improved insufflation-exsufflation system for removal of broncho-pulmonary secretions with automatic triggering of the inhalation phase. There is a conduit for connection to a patient's airway and a pressure source with a positive pressure port and negative pressure port. A switching device selectively connects the conduit to the positive pressure port, the negative pressure port and a dwell port. A sensor system senses an inhalation by the patient. A controller system drives the switching device to connect the conduit sequentially to the positive port, the negative port and the dwell port and to return again to the positive port in response to the sensor system sensing an inhalation by the patient while the conduit is connected to the dwell port.

In a preferred embodiment the switching device may include a selector valve or valves and an actuator device. The sensor system may include a pressure sensor in the conduit or an airflow detector. The controller system may include a programmed timer.

BRIEF DESCRIPTION OF THE DRAWINGS

Other objects, features and advantages will occur to those skilled in the art from the following description of a preferred embodiment and the accompanying drawings, in which:

FIGS. 2 and 3 are schematic diagrams showing alternative connections of the system to a patient's airway.

FIG. 4 shows an alternative embodiment of a sensor system employing a flow sensor.

DISCLOSURE OF THE PREFERRED EMBODIMENT

Figure 1:
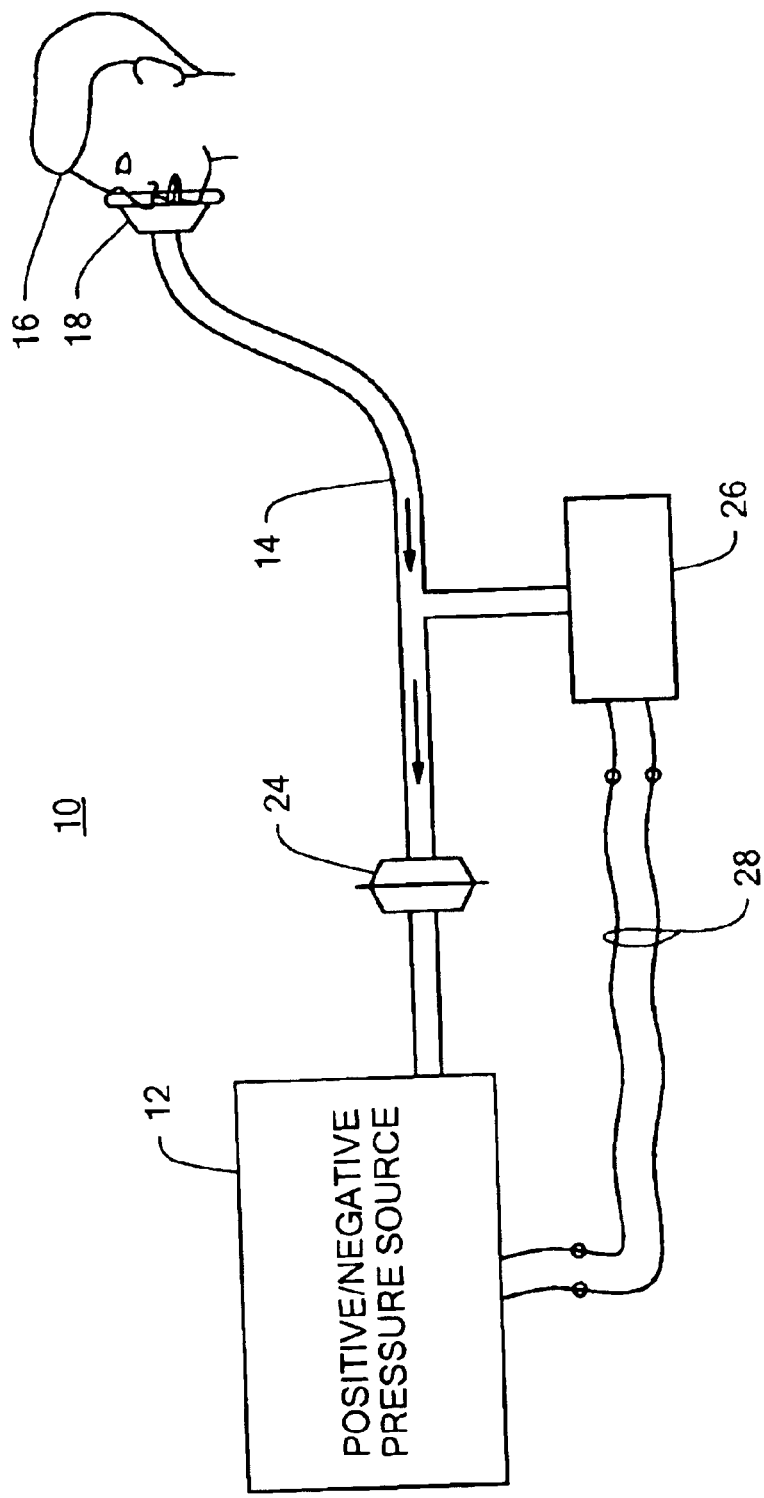
FIG. 1 is a schematic block diagram of an insufflation-exsufflation system according to this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

There is shown in FIG. 1 an improved insufflation-exsufflation system 10 according to this invention, including a positive/negative pressure source 12 and a conduit 14 through which it provides the positive and negative pressure to patient 16 through, for example, a face mask 18. Alternatively, conduit 14, FIG. 2, may be connected directly to a tracheostomy tube 20 or as shown in FIG. 3, to an endotracheal tube 22. A bacterial filter 24 may be employed in various location in conduit 14. A pressure transducer or pressure switch 26 may be employed to sense the pressure in conduit 14. When it senses a slight negative pressure indicative of an inhalation it provides a signal to pressure source 12 to provide the positive pressure flow to assist in the inhalation by the patient 16 and provides a signal over line 28. Alternatively, pressure transducer or pressure switch 26 may be replaced by a flow sensor 26a, FIG. 4, or any other suitable device which can sense the beginning of an inhalation by patient 16, for example, electrodes, strain gauges, or chest strap devices may be put on or around the patient's body or chest cavity to sense the beginning of an inhalation independent of the actual airflow characteristics in the airway of the patient.

Figure 5:
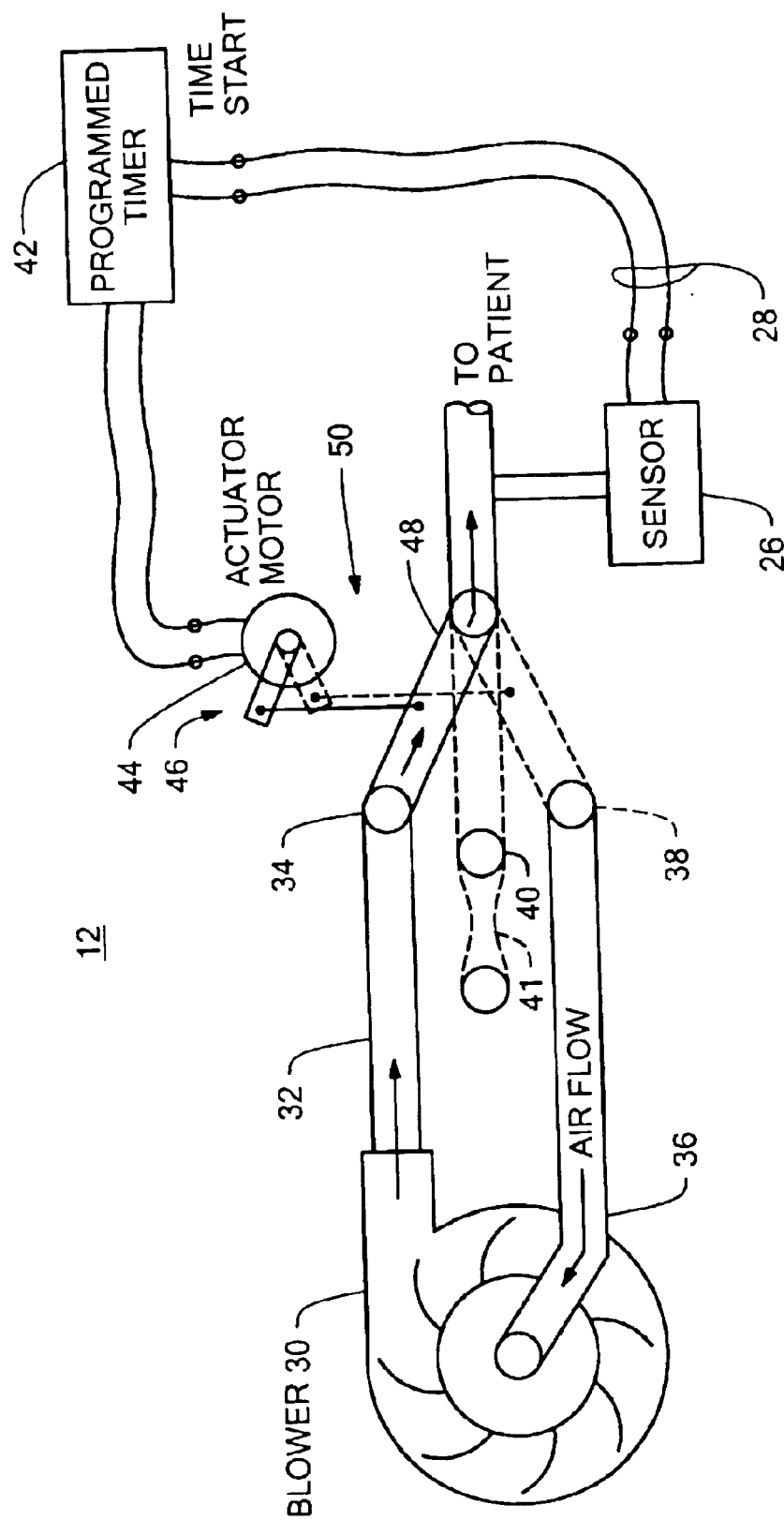
FIG. 5 is a more detailed schematic diagram of the positive/negative pressure source of FIG. 1.
Figure 6:
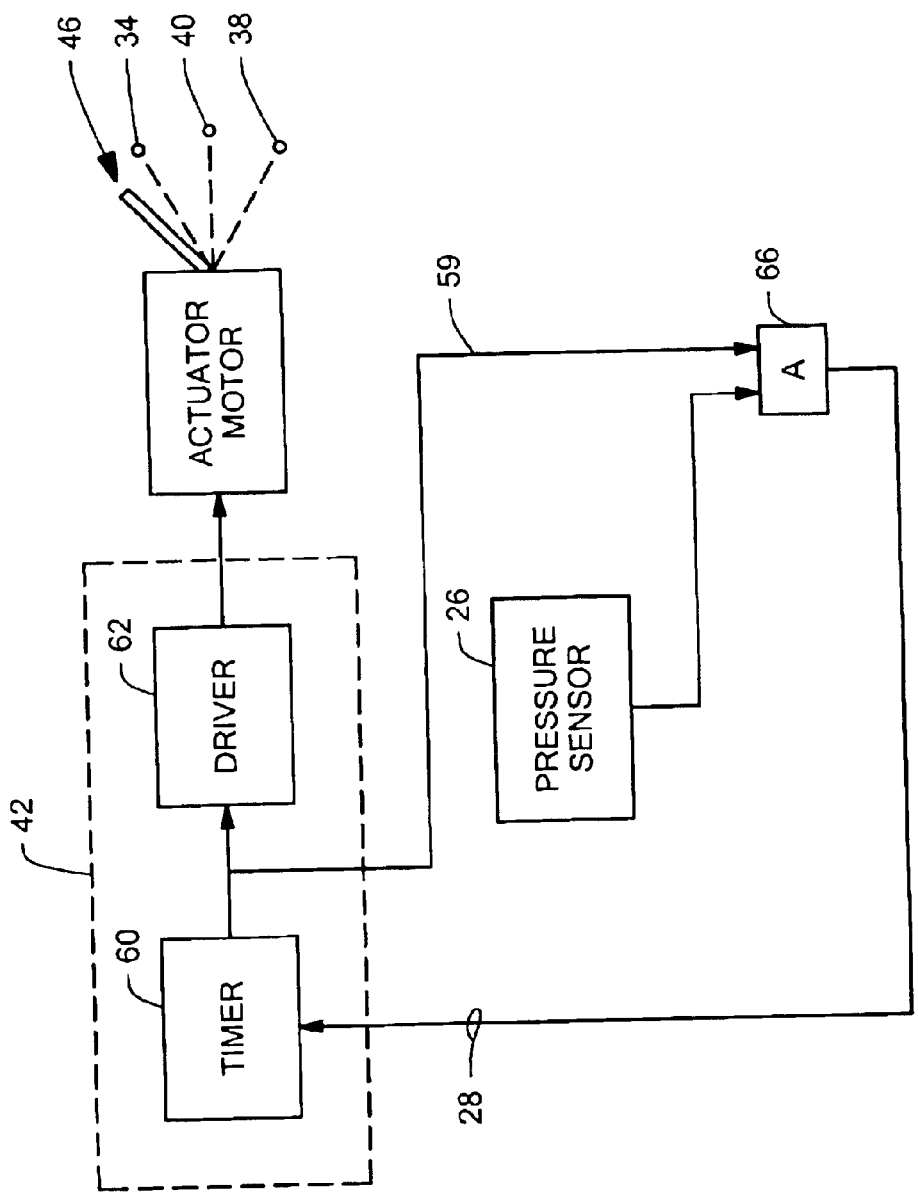
FIG. 6 is a schematic diagram showing in more detail the program timer of FIG. 5.

Pressure source 12, FIG. 5, may include a conventional blower 30 which provides a positive pressure during the inhale cycle in line 32 at positive pressure port 34 and a negative pressure during exhale in line 36 at negative pressure port 38. Dwell port 40 is provided for connection to ambient or atmospheric pressure, and may also include a flow restrictor 41 to make the sensor 26 more sensitive when it is, for example, a pressure sensor or pressure switch. Programmed timer 42, FIG. 5, drives actuator device or actuator motor 44 which through eccentric drive 46 moves swinger 48 of slider valve 50 from positive port 34 to negative port 38, then to dwell port 40. Swinger 48 remains there until sensor 26 senses that a patient inhalation has begun, at which point it sends a signal on line 28 to program timer 42 to once again operate actuator motor 44 to move slider switch 50 through the cycle of positive port 34, negative port 38 and dwell port 40. Programmed timer 42 may include a timer 60, FIG. 6, which operates driver circuit 62 that causes actuator motor 44 to step through the three positions of swinger 48: positive port 34, negative port 38, and dwell port 40. An alternate output 59 of the timer 60 (or of driver 62) indicates when the driver 62 is holding the swinger 48 at the dwell port 40, and provides one input to AND gate 66. When pressure sensor 26 senses that a patient inhalation is beginning it also provides an input to AND gate 66. When both those inputs are present at AND gate 66 it provides an output on line 28 to timer 60 to start the cycle again beginning with connection of swinger 48 to positive port 34.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the

What is claimed is:

1. An improved insufflation-exsufflation system for removal of broncho-pulmonary secretions with automatic triggering of inhalation phase comprising:

a conduit for connection to a patient's airway;

a pressure source with a positive pressure port, a dwell port and a negative pressure port;

a switching device for connecting said conduit to one of said positive pressure port, said negative pressure port or said dwell port;

a sensor system for sensing an inhalation by the patient; and a controller system for driving said switching device to connect said conduit sequentially to said positive port, said negative port and said dwell port and to return again to said positive port in response to said sensor system sensing an inhalation by the patient when said conduit is connected to said dwell port.

2. The improved insufflation-exsufflation system of claim 1 in which said switching device includes a selector valve and an actuator device.

3. The improved insufflation-exsufflation system of claim 1 in which said sensor system includes a pressure sensor in said conduit.

4. The improved insufflation-exsufflation system of claim 1 in which said sensor system includes an airflow detector in said conduit.

5. The improved insufflation-exsufflation system of claim 1 in which said controller system includes a programmed timer.

6. The improved insufflation-exsufflation system of claim 1 in which said dwell port is connected to atmospheric pressure.

7. The improved insufflation-exsufflation system of claim 1 in which said dwell port includes a restrictor portion to increase sensitivity.

* * * * *